US007676276B2

(12) United States Patent
Karell

(10) Patent No.: US 7,676,276 B2
(45) Date of Patent: Mar. 9, 2010

(54) STIMULATOR COMBINED WITH AN INTRANASAL RESPIRATORY METHOD AND DEVICE FOR IMPROVED BREATHING

(76) Inventor: Manuel L Karell, 1084 Jost La., Alameda, CA (US) 94502

( * ) Notice: Subject to any disclaimer, the term of this patent is extended or adjusted under 35 U.S.C. 154(b) by 301 days.

(21) Appl. No.: 11/772,250

(22) Filed: Jul. 2, 2007

(65) Prior Publication Data
US 2009/0012573 A1 Jan. 8, 2009

(51) Int. Cl.
*A61N 1/18* (2006.01)
(52) U.S. Cl. ............... 607/135; 607/2; 607/42; 607/134; 128/848
(58) Field of Classification Search ............... 600/534, 600/545; 128/848; 607/42, 134, 135
See application file for complete search history.

(56) References Cited

U.S. PATENT DOCUMENTS

| 4,249,527 | A | 2/1981 | Ko |
| 4,830,008 | A | 5/1989 | Meer |
| 4,944,310 | A | 7/1990 | Sullivan |
| 5,284,161 | A | 2/1994 | Karell |
| 5,755,219 | A * | 5/1998 | Thornton ............... 128/201.18 |
| 5,792,067 | A | 8/1998 | Karell |
| RE36,120 | E | 3/1999 | Karell |
| 6,209,542 | B1 | 4/2001 | Thornton |
| 6,212,435 | B1 | 4/2001 | Lattner |
| 6,618,627 | B2 | 9/2003 | Lattner |
| 2005/0022821 | A1* | 2/2005 | Jeppesen ............... 128/848 |

FOREIGN PATENT DOCUMENTS

WO PCT/US2005/044888 12/2005

* cited by examiner

*Primary Examiner*—Carl H Layno
*Assistant Examiner*—Erica Lee

(57) ABSTRACT

A nasal respiratory device and method adapted to provide electrical stimulation comprising an intraoral holdfast having a neuromuscular stimulator with electrodes adapted to provide electrical stimulation to a user for improving breathing and treating a respiratory disorder. The device and method affords access to ambient atmosphere or may be connected pressure devices such as CPAP. The device and method may also contain an airway resistor.

11 Claims, 6 Drawing Sheets

STIMULATOR COMBINED WITH AN INTRANASAL RESPIRATORY METHOD AND DEVICE FOR IMPROVED BREATHING

CROSS REFERENCE TO RELATED PATENTS

Not Applicable

STATEMENT REGARDING FEDERAL SPONSORED RESEARCH AND DEVELOPMENT

Not Applicable

NAMES OF PARTIES TO JOINT RESEARCH AGREEMENT

Not Applicable

BACKGROUND OF THE INVENTION

1. Technical Field

The devices and methods described herein relate generally to the field of medicine and more particularly to the fields of sleep and pulmonary medicine being useful for the treatment of diseases of air flow including snoring, sleep apnea and other breathing disorders.

2. Background

The mechanism of collapse of the airway that occurs during some stages of sleep is due to a general relaxation of the muscles that stabilize the upper airway segment. Snoring, in general, is the vibration of relaxed respiratory structures. The obstructive sleep apnea (OSA) syndrome afflicts 3% of the general population and is due to episodic upper airway obstruction during sleep. Invasive treatments of OSA includes such surgical interventions as tracheostomy, uvalo-palatopharyngoplasty, and maxillo-facial reconstruction. In general, medical therapy has been unproductive. The current non-invasive standard for treatment of breathing disorders is Continuous Positive Airway Pressure (CPAP) either performed nasally and/or intraorally: for example, U.S. Pat. No. 4,249,527 to Ko and U.S. Pat. No. 4,944,310 to Sullivan demonstrate methods and devices for CPAP. Mask discomfort, nasal congestion, nasal dryness, eye irritation, leakage of air through the mouth or nose (CPAP requires the maintenance of pressure) are very common problems for patients new to CPAP and other high pressure systems. CPAP has very poor patient compliance.

The prior art also includes devices containing electrodes for treating respiratory conditions. There are two methods in which electromuscular stimulation can be applied to a patient; invasively or non-invasively. Invasive electrical stimulation of a muscle involves implanting one or more electrodes, either permanently or temporarily within the patient. Non-invasive electrical stimulation of the muscles in the upper airway involves placing an electrode in direct contact with a surface of the patient and passing a current through the surface tissues adjacent the electrode: for example, U.S. Pat. No. 4,830,008 to Meer exhibits electrical stimulation to nerves and U.S. Pat. No. 5,284,161 issued to Karell exhibits a device for increasing muscle tone with electrodes applied to the soft palate in a removable dental appliance.

Airway patency depends on the activity of the pharyngeal dilator muscles. Common sites of obstruction are behind the tongue and at the level of the soft palate; hence, the reason for electrical stimulation to the soft palate to increase muscle tone. The muscles of the tongue, especially the posterior fibers of the genioglossus, draw the base of the tongue forward and anteriorly. One or more of the muscles of the tongue and/or mouth and/or pharynx and/or larynx normally contract reflexively during inspiration. OSA sufferers experience reduced muscle tone during sleep as compared to non-OSA patients, thereby causing a reduction in airway patency. Stimulation of one or more of the above structures improves airway dilatation. Airways that would normally collapse during respiration remain open when the patient breathes through pursed-lips, which is helpful in chronic obstructive pulmonary disease (COPD) and other respiratory conditions. Pursing lips produces expiratory resistance via proximal obstruction, that is, (Positive Expiratory End Pressure, PEEP). Pursing lip therapy is commonly used in daily medical practice.

What is missing in the prior art is the combination use of electrical stimulation and nasal or oral respiratory methods and devices. A combination effect is beneficial. The prior art does include U.S. Pat. No. 5,792,067 to Karell that contains electrodes and an airway; however, the Karell patent lacks the ability to include the nasal cavity; it also lacks the ability to include resistance in air passageways.

The following are examples of prior art which may be useful in the understanding of the utility of the instant invention.

U.S. Pat. No. RE36120 to Karell entitled "SNOPPER—THE SNORING STOPPER ANTI-SNORING MOUTH DEVICE" is described and the entire disclosure of which is incorporated herein by reference.

U.S. Pat. No. 5,792,067 to Karell entitled "APPARATUS AND METHOD FOR MITIGATING SLEEP AND OTHER DISORDERS THROUGH ELECTROMUSCULAR STIMULATION" is described and the entire disclosure of which is incorporated herein by reference.

U.S. Pat. No. 6,212,435 to Lattner et al. entitled "INTRAORAL ELECTROMUSCULAR STIMULATION DEVICE AND METHOD" is described and the entire disclosure of which is incorporated herein by reference.

U.S. Pat. No. 6,618,627 to Lattner et al. entitled "INTRAORAL ELECTROMUSCULAR STIMULATION DEVICE AND METHOD" is described and the entire disclosure of which is incorporated herein by reference.

U.S. Pat. No. 6,209,542 to Thornton entitled "COMBINATION FACE MASK AND DENTAL DEVICE FOR IMPROVED BREATHING DURING SLEEP" is described and the entire disclosure of which is incorporated herein by reference.

International Patent Application PCT/US2005/044888 by Doshi et al. entitled "RESPIRATORY DEVICES AND METHODS OF USE" is described and the entire disclosure of which is incorporated herein by reference.

BRIEF SUMMARY OF THE INVENTION

Described herein are respiratory devices and methods for treating a variety of medical diseases through the combined use of intraoral and/or intranasal electrodes for increasing muscle tone, stimulating muscles and nerves, and respiratory devices including devices making use of resistance in air passageway orally or nasally. CPAP and other high pressure systems are also utilized. Resistive respiratory devices may be added to either or both the nasal passageway or the oral passageway. Some versions of these devices make use of expiratory resistance to mimic the effects of pursed-lip breathing with or without PEEP.

The respiratory methods and devices described herein are adapted to be removably secured in communication with a respiratory cavity. A respiratory cavity may be a nasal cavity (e.g., nostril or nasal passage) or an oral cavity (e.g., mouth or throat). The respiratory device comprises a nasal passageway, and an intraoral holdfast for removably securing the respiratory device in communication with the respiratory cavity. The holdfast contains one or more electrodes for contacting an intraoral and/or intranasal surface. Additionally, an air flow resistor in communication with the nasal passageway or intraoral airway may be added.

In one version of the instant invention, the respiratory method and device is in communication with a nasal cavity and the device is removably secured in place with an intraoral holdfast. The holdfast may be adapted to be secured to the upper or to the lower dentition of a user's mouth. A stimulator within the holdfast is connected to an electrode for contacting an intraoral and/or an intranasal surface. Any or all of the components of the device may be moldable for user comfort.

In another version of the instant invention, the respiratory method and device is in communication with a nasal cavity and the device is removably secured in place with an intraoral holdfast. The holdfast is composed of two components; an upper dentition member and a lower dentition member, wherein the members may be positioned to improve airway patency. A stimulator within the holdfast is connected to an electrode for contacting an intraoral and/or an intranasal surface. Any or all of the components of the device may be moldable for user comfort.

In another version of the instant invention, the respiratory method and device is in communication with a nasal cavity and the device is removably secured in place with an intraoral holdfast. The holdfast additionally comprises a tongue holding means for holding the tongue in a position to increase airway patency. A stimulator within the holdfast is connected to an electrode for contacting an intraoral and/or an intranasal surface. Any or all of the components of the device may be moldable for user comfort.

Any or all versions may have an intraoral holdfast that includes an airway.

Any or all versions may have an intraoral holdfast that includes of tongue holding means for pulling the tongue anteriorly thereby increasing patency in the respiratory tract.

Additionally, any or all versions may include an air flow resistance means. The air flow resistance may be orally and/or nasally performed. Virtually any type of air flow resistor may be used with the respiratory devices described herein, including flap valves, membrane valves, hingeless valves, balloon valves, stopper-type valves, ball valves, and the like. air flow resistance may be one-way or two-way and may be controllable.

DETAILED DESCRIPTION OF THE INVENTION

Figure 1A:
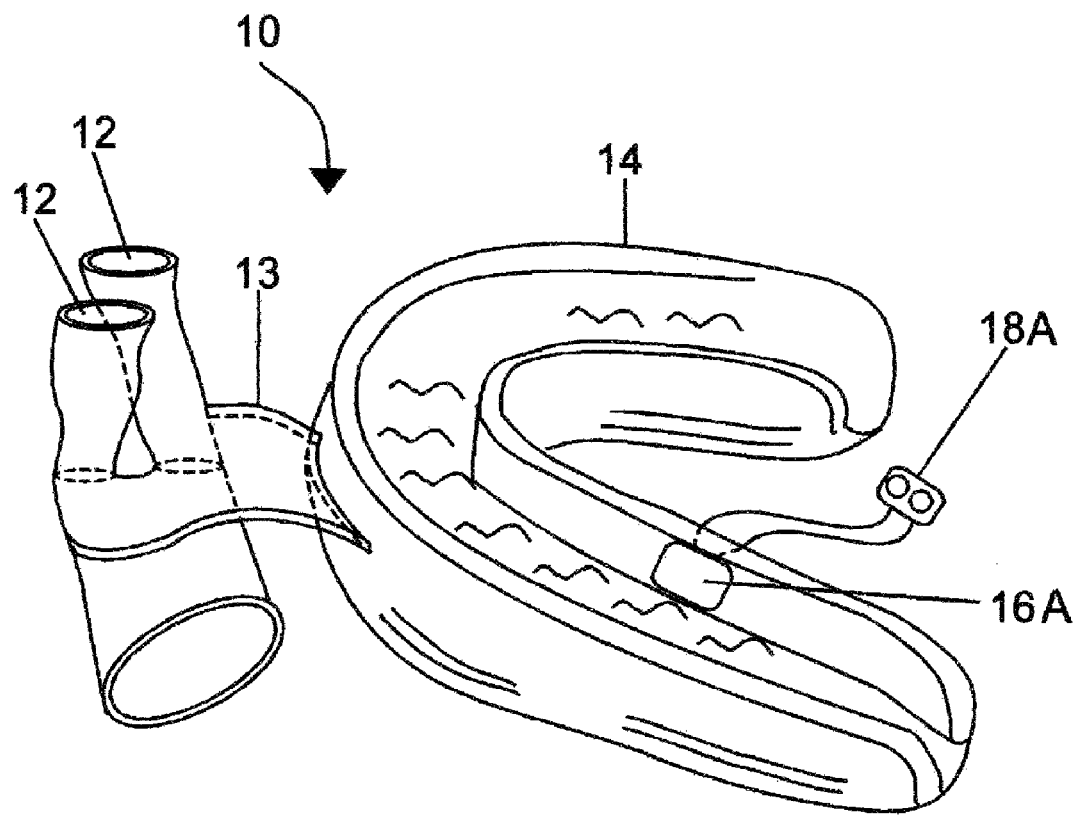
FIG. 1A is a perspective view of a nasal respiratory device with an intraoral holdfast having a stimulator and an intraoral electrode.
Figure 1B:
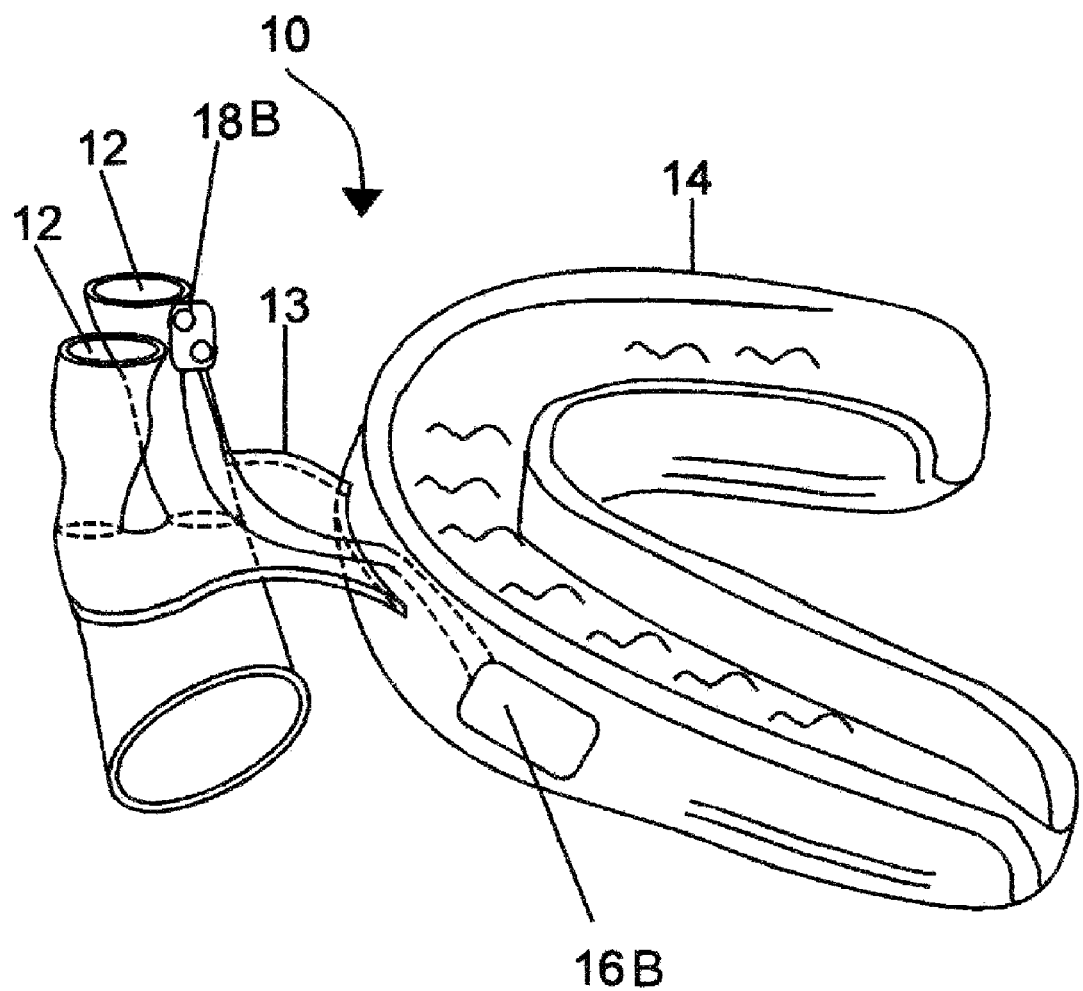
FIG. 1B is a perspective view of a nasal respiratory device with an intraoral holdfast having a stimulator and an intranasal electrode.

Referring to FIGS. 1A and 1B there is a general representation of the instant invention 10 of a nasal respiratory device adapted to provide electrical stimulation to a user to reduce or minimize the occurrence of a breathing disorder. Referring to FIG. 1A a nasal passageway 12 is connected 13 to a holdfast 14 adapted to be inserted into a user's mouth thereby securing the nasal passageway 12. The holdfast 14 is depicted as fitting over an upper dentition. The holdfast contains a neuromuscular stimulator 16A (or 16B in FIG. 1B) which is attached to at least one electrode 18A which is shown in FIG. 1A as intraorally placed electrode whereas in FIG. 1B the electrode 18B is shown as intranasally placed electrode. The user inserts nasal passageway 12 into his (or her) nostril(s) and inserts the holdfast 14 into his (or her) mouth. The intraoral holdfast removably secures the nasal passageway. The stimulator 16A (or 16B in FIG. 1B) is activated and energizes the electrode 18A which is in contact with an intraoral (or intranasal 18B) surface. The energized electrode stimulates muscles or nerves or mucous membranes or skin to enhance respiratory patency. Additionally, the nasal passageway may be connected to CPAP. (not shown)

Figure 2:
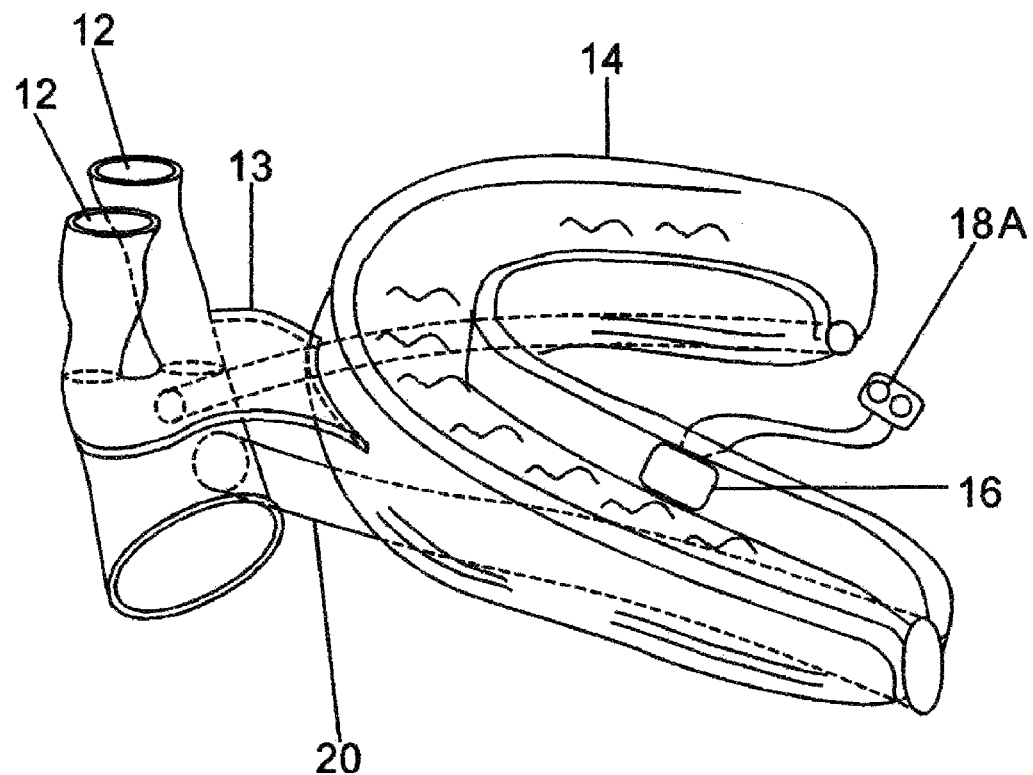
FIG. 2 is a perspective view of a respiratory device with an intraoral holdfast additionally having an airway.

Referring to FIG. 2 the holdfast 14 additionally having an airway 20. CPAP may also be utilized via the airway. (not shown)

Figure 3:
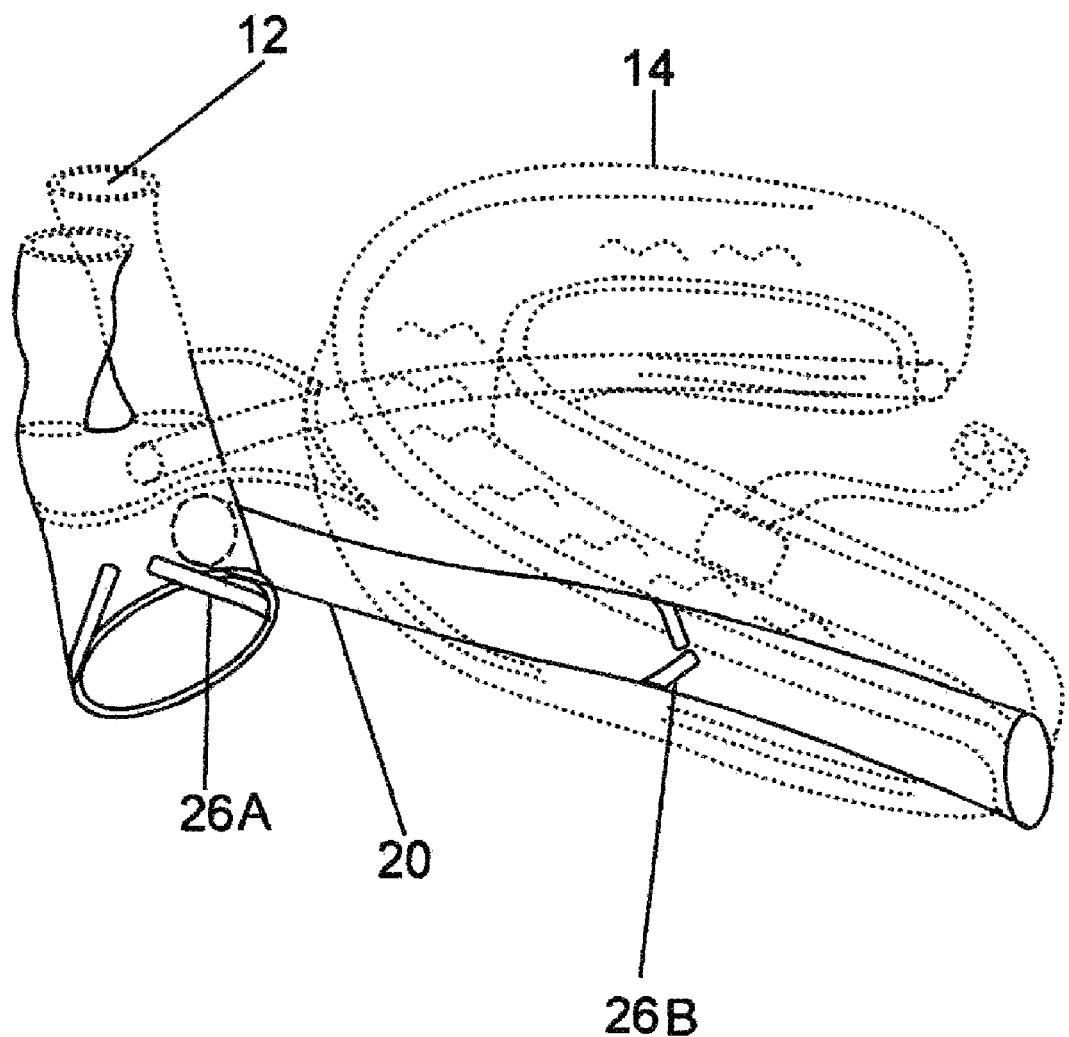
FIG. 3 is a perspective view of a nasal passageway and/or an intraoral airway additionally having an air flow resistor.

Referring to FIG. 3 the nasal passageway 12 and the airway 20 having air flow resistors 26A and 26B. The air flow resistor has similar clinical effects as does pursing lip therapy in treating respiratory disorders such as COPD. The air flow resistor may be one or many. The air flow resistor may be in the nasal passageway and/or the holdfast. The addition of air flow resistor decreases the pressure required when CPAP is utilized.

Figure 4:
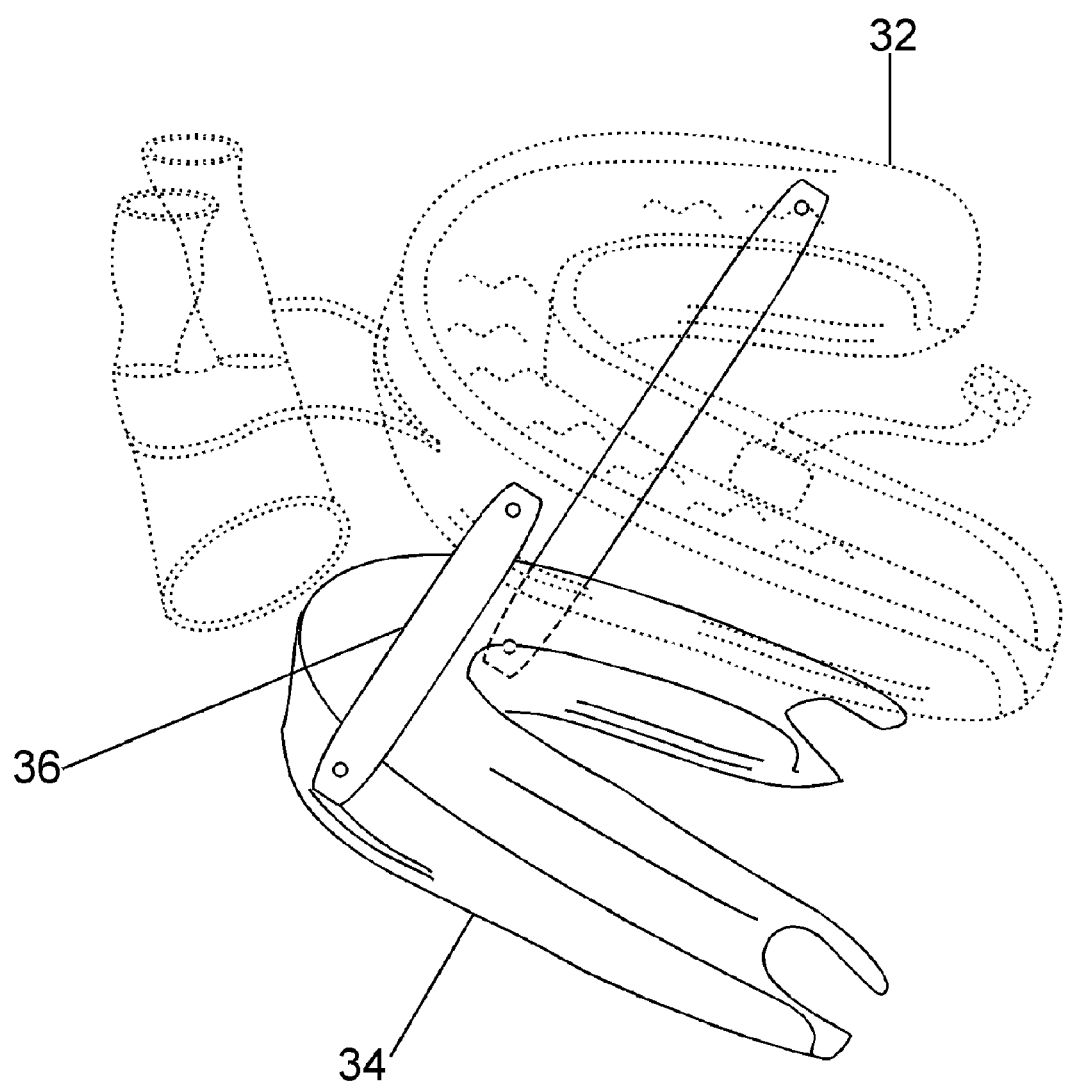
FIG. 4 is a perspective view of a respiratory device having a holdfast with two members which are adjustable in relation to each other.

Referring to FIG. 4 a holdfast comprising two components: an upper dentition member 32 and a lower dentition member 34 operably connected by a connecting assembly 36. Generally speaking, a user will position the lower member to protrude relative to the upper member thereby enhancing the respiratory space.

Figure 5:
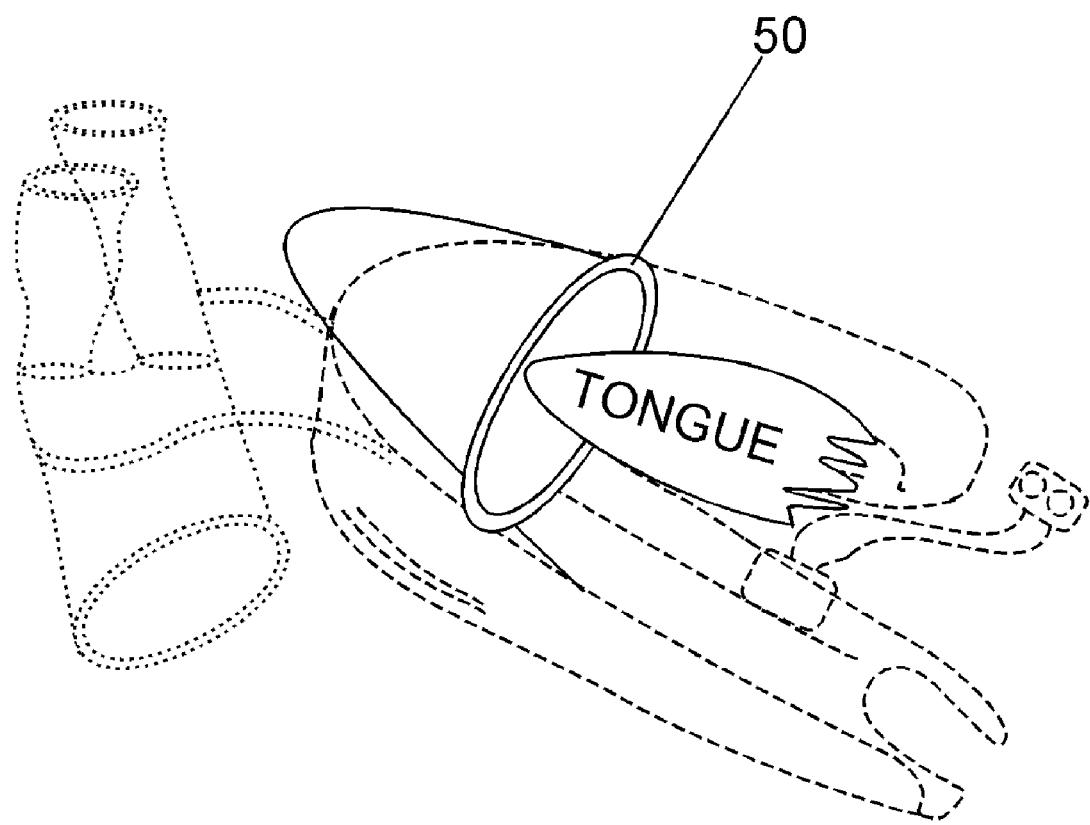
FIG. 5 is a perspective view of a respiratory device having a holdfast capable of holding the user's tongue in a position to improve respiratory tract patency.

Referring to FIG. 5 a holdfast additionally having a tongue holding means 50 in which the user's tongue is pulled forward to enhance the respiratory space.

The above detailed description illustrates the invention by way of example, not by way of limitation of the principles of the invention. This description will clearly enable one skilled in the art to make and use the invention.

What I claimed:

1. A nasal respiratory device adapted to provide electrical stimulation intranasally to a user comprising:
    a passageway means for sealed air communication with a user's respiratory system;
    a holdfast means for removably securing said nasal respiratory device operatively connected to said passageway means;
    at least one neuromuscular stimulator means for providing electrical stimulation operatively connected to said holdfast means;
    and at least one electrode means for contacting the user intranasally, operatively connected to and deriving energy from said neuromuscular stimulator means.

2. A nasal respiratory device of claim 1 wherein said holdfast means additionally comprises at least one airway means for allowing air flow operatively communicating with said passageway means.

3. A nasal respiratory device of claim 1 or claim 2 wherein said holdfast means is adapted to engage a user's upper or a user's lower dentition or to engage with structures associated with the dentition.

4. A nasal respiratory device of claim 1 or claim 2 wherein at least one air flow resistor means is in communication with said passageway means or said airway means for increasing resistance to air flow.

5. A nasal respiratory device of claim 4 wherein said air flow resistor means increases the resistance to air exhaled through the passageway means or airway means but does not substantially increase the resistance to air inhaled through the passageway means or airway means.

6. A nasal respiratory device of claim 1 or claim 2 wherein said holdfast means comprises:
- a first member adapted to engage a structure associated with a user's upper dentition;
- a second member adapted to engage a structure associated with a user's mandible;
- a connecting assembly connecting the first member and the second member so as to limit movement of the first member relative to the second member, thereby controlling a position of the user's mandible relative to the upper dentition.

7. A device of claim 1 or claim 2 wherein said holdfast additionally comprises a tongue holding means for holding the tongue of a user in a position to enhance patency of the user's respiratory tract.

8. A device of claim 6 wherein said holdfast additionally comprises a tongue holding means for holding the tongue of a user in a position to enhance patency of the user's respiratory tract.

9. A method for providing sealed air flow with intranasal electrical stimulation in an upper airway system of a user, said method comprising the steps of:
- providing a nasal passageway operatively connected to a holdfast having a neuromuscular stimulator operatively connected to one or more intranasal electrodes;
- inserting said nasal passageway and said holdfast into the user;
- additionally having said one or more electrodes contact the user intranasally; and
- then providing electrical stimulation to enhance air flow to the user.

10. Method according to claim 9 wherein continuous positive air pressure (CPAP) is additionally provided and wherein the user inserts the CPAP into said sealed air flow.

11. A method according to claim 9 wherein additionally provided is the further step of inserting an air flow resistor into the nasal passageway for mimicking pursed lip breathing in the user.

\* \* \* \* \*